US005767104A

United States Patent [19]
Bar-Shalom et al.

[11] Patent Number: 5,767,104
[45] Date of Patent: *Jun. 16, 1998

[54] USE OF SULFATED SACCHARIDES TO TREAT BALDNESS

[76] Inventors: Daniel Bar-Shalom, Rypevanenget 213, DK-2980 Kokkedale; Niels Bukh, Strandvejen 122, DK-2900 Hellerup, both of Denmark

[ * ] Notice: The term of this patent shall not extend beyond the expiration date of Pat. No. 5,618,798.

[21] Appl. No.: 460,143

[22] Filed: Jun. 2, 1995

Related U.S. Application Data

[63] Continuation of Ser. No. 247,478, May 23, 1994, Pat. No. 5,618,798, which is a continuation of Ser. No. 47,078, Apr. 16, 1993, abandoned, which is a continuation of Ser. No. 613,559, filed as PCT/DK90/00104, Apr. 19, 1990, abandoned, which is a continuation-in-part of Ser. No. 407,236, Sep. 14, 1989.

[30] Foreign Application Priority Data

Apr. 20, 1989 [DK] Denmark .................... DK1918

[51] Int. Cl.$^6$ .................... A61K 31/70
[52] U.S. Cl. .................... 514/53; 514/23; 514/25; 514/54
[58] Field of Search .................... 514/53, 54, 23, 514/25

[56] References Cited

U.S. PATENT DOCUMENTS 4,912,093   3/1990   Michaeli .................... 514/53

FOREIGN PATENT DOCUMENTS 211610   2/1987   European Pat. Off. .

OTHER PUBLICATIONS

Caseso et al, Chemical Abstracts, vol. 105 (1986) No. 66249f.
Couclman et al, Chemical Abstracts vol. 108 (1988) No. 56539Y.
The Merk Manual of Diognosis and Therapy 5th. ed. (1987) pp. 2281–2282.

*Primary Examiner*—Elli Peselev
*Attorney, Agent, or Firm*—Iver P. Cooper

[57] ABSTRACT

A method of treating and/or preventing alopecia (baldness, deficient hair growth) comprises administering to a patient in need thereof a therapeutically or prophylactically effective amount of a sulfated mono-, di- or oligosaccharide or a derivative, salt or complex thereof. The saccharide is preferably polysulfated, such as a polysulfated disaccharide, in particular sucrose, or a derivative, complex or salt thereof. Especially interesting polusulfated disaccharides are sucrose pentasulfate, sucrose hexasulfate, sucrose heptasulfate and sucrose octasulfate, e.g. in the form of a potassium or sodium salt, or in the form of sucralfate.

23 Claims, No Drawings

USE OF SULFATED SACCHARIDES TO TREAT BALDNESS

This is a continuation of application Ser. No. 08/247,478, filed May 23, 1994, now patented, U.S. Pat. No. 5,618,798, which is a continuation of application Ser. No. 08/047,078 filed Apr. 16, 1993, now abandoned, which is a continuation of application Ser. No. 07/613,559 filed Nov. 21, 1990, now abandoned, which was the national stage of PCT/DK90/00104, filed Apr. 19, 1990, which is a continuation-in-part of Ser. No. 07/407,236, filed Sep. 14, 1989, all of which are hereby incorporated by reference.

Alopecia (baldness or deficient hair growth) is a condition which leads to more or less disabling or discomfort to the individual suffering therefrom, ranging from minor cosmetic disadvantages to severe psychological consequences.

Alopecia has a number of etiologies.

The most common form of alopecia is androgenetic alopecia, more accurately described as common baldness. Androgenetic alopecia occurs in chimpanzees, orangoutangs and other primates as well as in man.

As is implied by the name, androgenetic alopecia is induced by androgenic stimulation of hair follicles predisposed by the interdependent influences of genetic factors and of ageing. Despite its name, it affect both the male and the female.

The initial stage in the condemned follicles is probably the accumulation of 5α-dihydrotestosterone, the tissue-active androgen which inhibits the metabolism of such follicles.

There is a marked racial variation in the incidence of androgenetic alopecia. The disease is most frequent and severe in Caucasoids.

The earliest histological change is the appearance of foci of degeneration in the lower part of the connective-tissue sheath of the follicles, with perivascular basophilic change. The follicle gradually shrinks, leaving beneath it a strand of sclerosed and hyaline connective tissue. However, even in areas of scalp in which almost all follicles are short and small, producing at best only tiny vellus hairs, there remain a few quiescent terminal follicles which can be stimulated into growth to give false hopes of a cure.

Androgenetic alopecia is a very widespread condition, at least in its less severe forms. Thus, during adolescence, uniform recession of the frontal hair-line occurs in 96% of males and about 80% of females.

As mentioned above, there are a number of other etiologies of alopecia, such as the administration of chemicals, such as drugs. As examples of these may be mentioned anticoagulants such as large doses of heparin, heparinoids and coumarins, cytostatic agents, triparanol and fluorobutyrophenone, excessive consumption of vitamin A, occupational exposure to sodium borate, potassium thiocyanate, large amounts of bismuth. Also, oral contraceptives have been suspected of giving rise to the disease, and the same applies to propranolol, metoprolol, levodopa, and ibuprofen.

Also, alopecia may have nutritional or metabolic origin, or it may be caused by disorders of the central nervous system. Furthermore, the significant association of the atrophic state with alopecia areata has been stressed relatively recently in some populations. Also, an association between autoimmunity and alopecia areata has long been recognized. Alopecia including areata is also often seen in association with skin disease such as scalp eczema, psoriasis and other dermatosis and also in association with systemic disease such as LE.

Today, no completely satisfactory treatment or prophylaxis of alopecia exists. Although topical administration of minoxidil can induce regrowth, it is not considered the definitive therapy.

Heparin, heparinoids and related glycosaminoglycans have been suggested as effective in stimulating hair growth (e.g. DE 3543221 A1, GB 936 916, GB 1 098 935, EP 35 919, EP 182 756, EP 277 428, EP 279 244, EP 295 092, EP 297 455).

In EP 295 092, it is described that hyaluronic acid fragments comprising from 7 to 50 monosaccharide units terminating either with a glucuronic acid unit and/or a N-acetyl glucosamine unit, or an unsaturated derivative of one or both of these terminal units are useful as hair stimulating agents when topically applied to the scalp. Such compounds can be characterized by being "naturally" occurring mucopolysaccharide moieties.

It has now surprisingly been observed that after 3–4 weeks of two daily applications of an ointment containing 10% w/w of sucralfate, there was appearance of hair in the otherwise bald lateral-frontal areas in a 40-year-old male who had a normal common male-pattern baldness. At the beginning, a "plume" appeared in the area, and after a few days the "plume" began turning into real hairs and 8 days after, there were dozens of real hairs which were indistinguishable from other hairs of the scalp, apart from being shorter and all coloured, in contrast to the existing hair, which was partially greyed.

This observation is most remarkable in view of the fact that sucralfate or sulfated mono-, di- or oligosaccharides have apparently not been suggested as means for treating or preventing alopecia. Also, the sulfated mono-, di- or oligosaccharides do not belong to any chemical or therapeutic group of compounds previously used or suggested for the treatment of alopecia, such as minoxidil, vitamin A, steroids, in particular triamcinolone, pyrimidine carbamate, squaric acid, allergens and psoralens in PUVA and naturally occurring mucopolysaccharides.

Sucralfate and other disaccharide polysulfate-aluminium compounds have been indicated as effective in alleviating the symptoms of anorectal disease when topically applied to human skin, and as effective in promoting the healing of wounds (WO 89/00047), and sulfated oligosaccharides, particularly mono- and disaccharides such as sucrose octasulfate, have been mentioned as wound healing agents (EP 230 023). WO 89/05645 and WO 89/05646 disclose a broad range of pharmacological effects of sucralfate and sucrose octasulfate anti-inflammatory, anti-infective, anti-malignant, skin-protective and anti-wrinkle and other effects after topical or systemic administration. WO 89/07932 discloses the use of sucralfate and sucrose octasulfate in the treatment of gingivitis and parodontosis.

Based upon the observations made in the present invention and the inventors' knowledge of sulfated saccharides, it is reasonable to contemplate that the hair growth stimulating effect will extend not only to sucralfate and the sodium salt of sucrose octasulfate, but also to other related sulfated mono-, di- and oligosaccharides, which are of a type not naturally occurring in glycosaminoglycan structures.

SUMMARY OF THE INVENTION

In one aspect, the invention provides a method of treating and/or preventing alopecia, the method comprising administering to a patient in need thereof a therapeutically or prophylactically effective amount of a sulfated mono-, di- or oligosaccharide or a derivative, salt or complex thereof.

In another aspect, the invention relates to the use of a sulfated mono-, di- or oligosaccharide for preparing a composition for use in the treatment and/or prevention of alopecia.

In a further aspect, the invention relates to the cosmetic use of a sulfated mono-, di- or oligosaccharide for combating or preventing hair loss and/or preserving the natural colour of the hair.

DETAILED DISCLOSURE OF THE INVENTION

The sulfated saccharide used in accordance with the invention may be a sulfated monosaccharide, for instance sulfated xylose, fructose, glucose, ribose, arabinose, galactose, rhamnose, fucose, sorbose, psicose, tagatose or gulose, a sulfated disaccharide such as sulfated sucrose, lactose, maltose or cellobiose, or a sulfated oligosaccharide such as sulfated maltotriose, maltertreose, or a sulfated raffinose, which is an oligosaccharide comprising a sulfated sucrose moiety together with a galactose moiety, or a sulfated melezitose, which is a sulfated sucrose moiety together with a glucose moiety. In the present context, the term "an oligosaccharide" is a saccharide consisting of 3–20 monosaccharide units in accordance with the generally accepted terminology.

The sulfated mono-, di- or oligosaccharide is preferably a polysulfated or persulfated saccharide, which means that two or more, possibly all, sulfur-containing moieties are present as substituents on hydroxy groups of the carbohydrate moiety.

In some cases, the sulfated mono-, di- or oligosaccharide may be complexed with or form a salt with a metal, e.g. an alkali or alkaline earth metal such as Na, K, Ca, Mg or Ba, or Al, Zn, Cu, Zr, Ti, Bi, Mn or Os, or with an organic base (e.g. an amino acid). The currently preferred salts are potassium and sodium salts, and the preferred complex is the aluminium complex. Furthermore, the mono-, di- or oligosaccharide may be in the form of a suitable derivative, e.g. a mono-, di- or polyester of aliphatic carboxylic acids such as formic, acetic, propionic, butanoic, myristic or stearic acid.

Preferably, the composition of the invention contains a persulfated disaccharide, for example sucrose octasulfate.

The preferred sulfated disaccharide can be represented by the following formula:

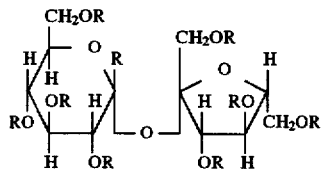

wherein R is H, $SO_3[Al_2(OH)_5]$, $SO_3H$ or an acyl residue of the above-mentioned carboxylic acids, the groups designated R being the same or different, with the proviso that at least one R represents a sulfate group, or physiologically acceptable salts or complexes thereof.

The particular preferred compounds according to the invention are sucralfate and the potassium or sodium salt of sucrose octakis(hydrogen sulfate).

Sucralfate may also be termed sucrose octakis(hydrogen sulfate) aluminium complex. Its CAS number is 54182-58-0. The commercial product is a white powder which is practically insoluble in water and most organic solvents; it is soluble in acids and alkalis. In practice, there may be slight variations in the chemical composition, e.g., due to the fact that the sulfation may be slightly incomplete so that the product may, e.g., contain a certain proportion of molecules which are not octasulfated (persulfated), but rather less sulfated such as heptasulfated. Such minor variations in the commercial product are well known and are reflected in the fact that e.g., the aluminium content in commercial products may range from 17 to 21% and sulfur from 9.5 to 12.5%. In the present context, the term "sucralfate" also comprises such generally accepted minor variations.

Sucralfate may, for instance, be prepared as disclosed in U.S. Pat. No. 3,432,489 by reacting a 1–10% w/w aqueous solution of sucrose octasulfate or an alkali metal or alkaline earth metal salt thereof with a 1–10% w/w aqueous solution containing aluminium ions, preferably $AlCl(OH)_2$ at room temperature and a pH of 4–4.5. The sucrose octasulfate may be prepared by reacting sucrose with $ClSO_3H$, $H_2SO_4$ or $H_2SO_4$—$C_5H_5N$.

The sulfated saccharides may otherwise be prepared, for example, as disclosed in EP 230023.

The sulfated sucrose is preferably selected from the group consisting of sucrose pentasulfate, sucrose hexasulfate, sucrose heptasulfate and sucrose octasulfate.

The administration form in which the sulfated saccharide is administered will normally be a form suitable for topical application to the affected area. However, also administration into the skin or administration under the skin, e.g. by injection (by needle or dermajet) or other methods, are contemplated.

Although there may be cases where the sulfated saccharide may be administered as such, it will typically be compounded with one or more pharmaceutically acceptable carriers or excipients to present it in a form which is suitable for topical application or for injection or other form of introduction into or under the skin. In other words, it will be in e form of a liquid, semi-solid or solid topical or systemic preparation such as an ointment, lotion, gel, cream, emulsion, solution, suspension, microemulsion, liposomes or as a rollball applicator, sponge applicator or a spray device; a shampoo, hair tonic, hair conditioner, soap, balm, spray, paste, powder, sponge, strip, plaster, pad, dressing, or a comb or brush impregnated with or carrying the sulfated saccharide in such a manner that it is released when the comb or brush is used at the affected area.

The above-mentioned compositions are also suitable for cosmetic purposes where the compositions are applied to the hair or the skin areas normally covered with hair in order to prevent hair loss and/or to preserve the natural colour of the hair. Preferred compositions for cosmetic use are e.g. gels, emulsions, suspensions, liposomes, shampoos, hair tonics, hair conditioners, soaps, balms or sponges.

It may be interesting in certain cases to combine the sulfated saccharide with other forms of therapy, in particular therapies known to either produce hair growth by themselves such as vitamin A, minoxidil, squaric acid, allergens, irritants, corticosteroids, or agents which attack or modify the mechanism responsible for the alopecia, such as in the case of fungal infection, an ointment containing sucralfate and an antifungal agent such as ketoconazole, miconazole, clotrimazole, antiviral agents, such as acyclovir, antiinflammatory agents, antibacterial agents, etc. Also, it may advantageous to combine the sulfated saccharide with other pharmaceutical products known to have beneficial effects on the skin, such as vitamins, including vitamins B, vitamin E, lactic acid, astringents, emollients, or other agents, such as hyaluronic acid or other glycosaminoglycans, dermatan sulfate, chondroitin sulfate, keratan sulfate, heparan or heparan sulfate. Normally, the sulfate saccharide will be the predominant active component of the preparation.

Furthermore, advantages may be achieved by incorporating pharmaceutically acceptable amounts of penetration enhancers in the formulations, such as salicylic acid and other keratolytics, amino acids, thioglycollates, dimethylsulfoxide, and hydrating agents, such as glycerol.

Plasters, sponges, strips, pads or other dressings may be prepared by impregnating a dressing material such as cotton wool or gauze or a polymeric substance with a solution or suspension of the sulfated saccharide followed by drying. Alternatively, a paste, lotion, cream or gel containing the sulfated saccharide may be spread over the dressing material.

Alternatively, the sulfated mono-, di- or oligosaccharide may in certain cases be injected or otherwise introduced into or under the skin or scalp.

For topical application, the preparation may be formulated in accordance with conventional pharmaceutical practice with pharmaceutical excipients conventionally used for topical applications. The nature of the vehicle employed in the preparation of any particular composition will depend on the method intended for administration of that composition. Vehicles other than water that can be used in compositions can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, cetyl a isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

solvents, such as water, methylene chloride, isopropanol, castor oil, ethylene glycol monoethyl ether, diethylene glycol monobutyl ether, diethylene glycol monoethyl ether, dimethyl sulfoxide, tetrahydrofuran, vegetable and animal oils, glycerol, ethanol, propanol, propylene glycol, and other glycols or alcohols, fixed oils;

humectants, such as glycerin, sorbitol, sodium 2-pyrrolidone-5-car-boxylate, soluble collagen, dibutyl phthalate, gelatin;

powders, such as chalk, talc, kaolin, starch and derivatives thereof, gums, colloidal silicon dioxide, sodium polyacrylate, chemically modified magnesium aluminium silicate, hydrated aluminium silicate, carboxyvinyl polymer, sodium carboxymethyl cellulose, ethylene glycol monostearate;

gelling or swelling agents, such as pectin, gelatin and derivatives thereof, cellulose derivatives such as methyl cellulose, carboxymethyl cellulose or oxidised cellulose, guar gum, acacia gum, karaya gum, tragacanth gum, bentonite, agar, carbomer, bladderwrack, ceratonia, dextran and derivatives thereof, ghatti gum, hectorite, ispaghula husk, xanthan gum;

polymers, such as polylactic acid or polyglycolic acid polymers or copolymers thereof, paraffin, polyethylene, polyethylene oxide, polyethylene glycol, polypropylene glycol, polyvinylpyrrolidone; surfactants, such as non-ionic surfactants, e.g. glycol and glycerol esters, macrogol ethers and esters, sugar ethers and esters, such as sorbitan esters, ionic surfactants, such as amine soaps, metallic soaps, sulfated fatty alcohols, alkyl ether sulfates, sulfated oils, and ampholytic surfactants and lecitins;

buffering agents, such as sodium, potassium, aluminium, magnesium or calcium salts (such as the chloride, carbonate, bicarbonate, citrate, gluconate, lactate, acetate, gluceptate or tartrate).

The preparation of the invention may also contain other additives such as stabilizing agents, preservatives, etc.

Furthermore, it may be advantageous to provide modified release preparations in which the sulfated saccharide is incorporated into a polymer matrix, or nanoparticles, or liposomes or micelles, or adsorbed on ion exchange resins, or carried by a polymer.

The pharmacologically active element in sucralfate is probably the non-aluminium complexed sodium and/or potassium salt of sucrose octakis(hydrogen sulfate). Since such a salt is soluble in water, it would seem that a small particle size would be an important factor when preparing formulations of the sparingly soluble sucralfate. One way of achieving a small sucralfate particle size is by means of milling, grinding or disintegrating apparatus, e.g. a three roll mill, where the sucralfate powder is ground, preferably together with a suitable liquid vehicle having a viscosity adapted to effectively suspend the resulting fine particles, and preferably a relatively low vapour pressure so that no excessive evaporation with resulting agglomeration of the fine particles will occur, such as a polyalcohol, for example glycerin or polyethylene glycol, normally having a molecular weight in the range of 200–6000, such as PEG 400. The resulting preparation will normally contain up to 60–70% by weight of sucralfate particles with a fairly uniform particle size of about 5–10 µm or less (for 95% by weight of the sucralfate), the being substantially evenly suspended in the vehicle. Such a paste can then be further suspended in any suitable pharmaceutical preparation using well known pharmaceutical methods. Another starting point for a small particle size sucralfate formulation is sucralfate "filter cake", which is an intermediary product obtained from the synthesis of sucralfate. The "filter cake" comprises sucralfate with a content of water of about 50% by weight, and with a particle size of about 5–10 µm or less. This material can be mixed with, for instance, a water-miscible liquid which has a relatively low vapour pressure, such as glycerin, in order to prevent the water from evaporating, and the sucralfate particles will retain their small size. Another important factor to take into consideration when preparing formulations of sucralfate and other sulfated saccharides is the strong negative charge of salts of sucrose octakis(hydrogen sulfate), and probably of most sulfated saccharides. The pharmacological effect of sucralfate, salts of sucrose octakis (hydrogen sulfate) and other sulfated saccharides probably depends on this negatively charged entity, and the pharmacological effect of the drug may be reduced by the presence of positively charged mono- and divalent ions in the vehicle. The person skilled in the art will be able to take this into consideration, using guidelines from the relevant literature, e.g., Martindale, The Extra Pharmacopoeia, The Pharmaceutical Press, London, or other pharmaceutical textbooks.

In this connection it should be mentioned that while the incorporation of sucralfate or other water-insoluble or sparingly water-soluble sulfated saccharides is best performed as described herein taking into consideration the physical and chemical properties of the sulfated saccharide, in particular the particle size considerations mentioned below, the incorporation of water-soluble sulfated saccharides, such as sodium and potassium salts of sucrose oktakis (hydrogen sulfate) in preparations discussed herein will normally be extremely simple and will ordinarily consist in the addition of the sulfated saccharide to the preparation or to constituents thereof in either dry or dissolved form.

The sulfated saccharide will normally be used in a preparation in an amount of 0.001–99%, typically about 0.1–75%, such as about 0.2–30%, preferably about 0.5–20%, such as about 2–20%, e.g., 3–15%, by weight of the total preparation. For therapeutic and/or prophylactic use, the sulfated saccharide may also be used in a preparation in an amount of about 0.001–99% w/w, typically about 0.01–50% w/w, such as about 0.05–30% w/w, preferably about 0.1–20% w/w, such as about 0.5–15% w/w.

The concentration of the sulfated saccharide to be used in each particular case will of course depend upon the type of preparation and the intended use, but also on the solubility characteristics of the sulfated saccharide and, for sparingly soluble and substantially insoluble sulfated saccharides, on the particle size thereof; the smaller the particle size, the faster will be the dissolution of even sparingly soluble or even substantially insoluble sulfated saccharides or complexes thereof. Insoluble or sparingly soluble salts or complexes of sulfated saccharides are preferably used in the form of a fine powder, for example having a particle size of 200 μm or less, such as 100 μm or less. Examples of very small particle sizes which may be desirable for certain purposes are e.g. 50 μm or less, such as 20 μm or less, in certain cases 10 μm or less, such as 5 μm or less.

A topical preparation containing the sulfated saccharide is normally administered between 1 and 10 times a day, depending on the formulation, the severity of the condition to be treated, the age of the patient, and other factors. Based upon experience with other substances used in the treatment of alopecia, in particular minoxidil, it is expected that the effect will depend on continuing application of the preparation, for several months, or even years. In view of the fact that sucralfate is remarkably free of side effects, there should be no adverse long term consequences of such a treatment.

The invention is further illustrated by the following non-limiting examples.

EXAMPLE 1

Preparation of Sodium and Potassium Sucrose Octasulfate

I. Sucrose Octasulfate 254.7 g (1.6 mol) of sulfur trioxide pyridine were slurried in 1300 ml of water-free pyridine. With stirring, 68.5 g (0.2 mol) of sucrose were added. The reaction mixture was heated to 65° C. and kept at this temperature for 240 minutes. As the reaction proceeded, the substance was separated as a thick flowing oil. When the reaction was terminated, the agitator was stopped, the pyridine phase was decanted, and the oily phase was dissolved in 600 ml of ion-exchanged water.

II. Potassium Sucrose Octasulfate

One portion of sucrose octasulfate solution prepared as described in I above was adjusted with 10% w/w aqueous potassium hydroxide to pH=9 with stirring at room temperature. The solution was evaporated at 50° C. in vacuo to remove pyridine and water until 880 g were left. The warm solution was filtered, adjusted to pH=9.5, and the substance was precipitated with slow cooling to 5° C. The substance was filtered and washed with 300 ml of 1:1 ion-exchanged water/methanol and 300 ml of methanol. The wet filter cake was dried in vacuo at 50° C. The crude product was dissolved at 40° C. in 700 ml of ion-exchanged water. The liquid was filtered and adjusted to pH=9.5, and the substance was precipitated with slow cooling to 5° C. The precipitated substance was filtered and washed with 300 ml of 1:1 ion-exchanged water/methanol and 300 ml of methanol. The wet filter cake was dried in vacuo at 50° C. The substance was reprecipitated twice as mentioned above.

Yield: 137 g (about 53%) of potassium sucrose octasulfate.

III. Sodium Sucrose Octasulfate

One portion of sucrose octasulfate solution prepared as described in I above was adjusted with 10% w/w aqueous sodium hydroxide to pH=9 with stirring at room temperature. The solution was evaporated at 50° C. in vacuo to remove pyridine and water. When 250 ml were distilled, 580 ml of ethylene glycol were added and the evaporation was continued until 10 mm vacuum. 100 ml of ethanol were added to the solution. The solution was filtered, and pH was adjusted to 9.5. 350 ml of ethanol were slowly added with vigorous stirring at 30°–35° C., and the substance will then precipitate. After the addition was ended, the mixture was cooled to 10° C., and the solid substance was filtered and washed with 50 ml of 1:1 ethanol/ethylene glycol and 200 ml of methanol. The wet filter cake was dried in vacuo at 50° C. The crude product was dissolved in 520 ml of ethylene glycol and heated to 40° C., and 100 ml of ethanol were added. The solution was filtered and pH was adjusted to 9.5. 350 ml of ethanol were slowly added with vigorous stirring at 30°–35° C. and the substance will then precipitate. After the addition was ended, the mixture was cooled to 10° C. and the solid substance was filtered. It was washed with 50 ml of 1:1 ethanol/ethylene glycol and 200 ml of ethanol. The wet filter cake was dried in vacuo at 50° C.. The substance was reprecipitated once as above and then dried for 2 hours at room temperature in 500 ml of ethanol. The substance was filtered, washed with 200 ml of ethanol and dried at 50° C. in vacuo.

Yield: 146 g (about 63%) of sodium sucrose octasulfate.

EXAMPLE 2

A cream consisting of the following ingredients is prepared (all percentages are by weight):

| | |
|---|---|
| 2:1 suspension of sucralfate* in polyethylene glycol 400 (10% sucralfate in the final product) | 15.0% |
| Lanolin | 10.0% |
| Vegetable oil (evening primrose oil) | 20.0% |
| Polyethylene glycol 400 monostearate | 10.0% |
| Water | to 100.0% |

*Sucralfate provided by Guilini Chemie, W. Germany.

The vegetable oil, lanoline and polyethylene glycol 400 monostearate were melted and thoroughly mixed with the warmed water to form an ointment. The sucralfate suspension was incorporated into the ointment.

EXAMPLE 3

A lotion is prepared from the following ingredients (all percentages are by weight):

| | |
|---|---|
| 2:1 suspension of sucralfate* in polyethylene glycol 400 (10% sucralfate in the final product) | 15.0% |
| Glycerol | 10.0% |
| Ethanol | 50.0% |
| Water | to 100.0% |

*Sucralfate provided by Guilini Chemie, W. Germany.

The ingredients were mixed together in the order stated to obtain a lotion.

EXAMPLE 4

A hair tonic is prepared from the following ingredients (all percentages are by weight):

| Sodium sucrose sulfate | 3.0% |
|---|---|
| Ethanol | 25.0% |
| Water | to 100.0% |

Sodium sucrose sulfate was dissolved in water and ethanol was then added to the solution.

EXAMPLE 5

A hair tonic is prepared as described in Example 4 from the following ingredients (all percentages are by weight):

| Sodium sucrose sulfate | 1.5% |
|---|---|
| Ethanol | 40.0% |
| Water | to 100.0% |

EXAMPLE 6

A lotion is prepared from the following ingredients (all percentages are by weight):

| Sodium sucrose sulfate | 0.5% |
|---|---|
| Isopropanol | 10.0% |
| Ethanol | to 100.0% |

EXAMPLE 7

A cream is prepared from the following ingredients (all percentages are by weight):

| Sodium sucrose sulfate | 2.0% |
|---|---|
| Cetyl alcohol | 6.0% |
| Mineral oil | 4.0% |
| Paraffin | 2.0% |
| Triethanolamine | 0.5% |
| Xanthan gum | 0.5% |
| Water | to 100.0% |

EXAMPLE 8

A lotion is prepared from the following ingredients (all percentages are by weight):

| Sucralfate | 5.0% |
|---|---|
| Hydroxyethyl cellulose | 0.5% |
| Ethanol | 25.0% |
| Propylene glycol | 40.0% |
| Water | to 100.0% |

EXAMPLE 9

A solution is prepared from the following ingredients (all percentages are by weight):

| Sodium sucrose sulfate | | 3.0% |
|---|---|---|
| Water | 50% | |
| Ethanol | 25% | to 100.0% |
| Propylene glycol | 25% | |

EXAMPLE 10

A shampoo is prepared from the following ingredients (all percentages are by weight):

| Propylene glycol oleate (PEG-55) | 1.5% |
|---|---|
| Sodium lauryl sulfate 28% | 23.0% |
| Cocamidopropyl bethaine | 9.0% |
| Dimethicone copolyol | 1.5% |
| Sodium sucrose octasulfate | 3.0% |
| NaCl | q.s. |
| Water | ad 100% |
| Phenopip (preservative) | 0.5% |

EXAMPLE 11

A mousse-conditioner is prepared from the following ingredients (all percentages are by weight):

| Glyceryl stearate (PEG-100 stearate) | 1.5% |
|---|---|
| Cetaryl alcohol | 1.5% |
| Dimethicone copolyol | 0.5% |
| Demineralized water | ad 100% |
| Phenopip (preservative) | 0.5% |
| Sodium sucrose octasulfate | 2.0% |

95% of the above mixture was placed in a spray bottle together with 5% of butane.

EXAMPLE 12

A skin lotion is prepared from the following ingredients (all percentages are by weight):

| Cire de lanol "seppic CTO" | 4.2% |
|---|---|
| Macrogoli stearas 400 "Simulsol M 45" | 1.8% |
| Arachidis oleum | 5.5% |
| Isopropyli myristas | 4.8% |
| Aqua purificata | 68.0% |
| Sucralfate, micronized (<5 micron) | 7.0% |
| Macrogolum 400 | 3.5% |
| Glycerolum 85% | 4.2% |
| Dil. paraoxibenzoas 10% | 1.0% |

EXAMPLE 13

A cream is prepared from the following ingredients:

| Paraffinum solidum | 19.6 mg |
|---|---|
| Cetanoleum | 196.0 mg |
| Cetomacrogolum 1000 | 196.0 mg |
| Vaselinum album | 588.0 mg |
| Acid. citricum monohydricum | 12.3 mg |
| Natrii citras | 32.5 mg |
| Propyleneglycolum | 56.0 mg |
| Aqua purificata | 1504.0 mg |
| Sucralfate, micronized (<5 micron) | 196.0 mg |

EXAMPLE 14

Effect of a treatment with sucralfate on common male-pattern baldness

The preparation of Example 2 was used in two daily topical applications by a 40-year-old male who had a normal, common male-pattern baldness. After 3–4 weeks, there was appearance of hair in the otherwise bald lateral-frontal areas in the scalp. At the beginning, a "plume" appeared in the area, and after a few days the "plume" began turning into real hairs and 8 days after, there were dozens of real hairs which were indistinguishable from other hairs of the scalp, apart from being shorter and all coloured in the original colour of the hair, in contrast to the existing hair, which was partially greyed.

EXAMPLE 15

Clinical evaluation of sodium sucrose sulfate in the treatment of alopecia. A pilot study During a 11 month period (April 1989 to March 1990), a total of 50 patients participated in a pilot study, evaluating the effect of the sodium salt of sucrose sulfate administered topically for the treatment of alopecia.

The test preparation was a 3% solution of Na-sucrose sulfate in a vehicle of 50% water/25% ethanol/25% propylene glycol (w/w), dispensed in 35 ml bottles with a sponge for topical administration on the scalp. The test preparation was applied morning and evening on the scalp, preferably on areas of partial or total alopecia. In average the patients have been using one bottle per month.

All patients were recruited by one dermatologist, and the effect of treatment was evaluated clinically by the same investigator, at monthly clinic visits.

The clinical effect was classified as very good in cases of definite cosmetic benefit, as good in cases of significant regrowth of new hair, but not to an extend that is cosmetically apparent at distance, and as no effect in cases of no or only marginal regrowth of hair.

Male androgenic alopecia was the clinical diagnosis in 35 patients, their age ranging from 17 years to 50 years. Period of treatment was about 3 months in 15 case, about 6 months in 10 cases, and about 9 months in 10 cases.

The following results were obtained:

| Age group (years) | No of patients | Clinical effect | | | |
|---|---|---|---|---|---|
| | | Very good | Good | No effect | Drop-outs |
| 17–25 | 20 | 8 | 8 | 4 | 0 |
| 25–40 | 10 | 4 | 2 | 2 | 2 |
| >40 | 5 | | 2 | 2 | 1 |

4 Patients in the age group 17–25 had previously failed on treatment with minoxidil (Regain®) and showed no effect on the test preparation. 4 Patients in the age group 25–40 had previously failed on treatment with minoxidil (Regain®) and all 4 showed a good effect on the test drug.

About 80% of the male androgenic alopecia suffered from milder to more severe seborrhea in the scalp, and both before and during the test drug period they received simultaneous treatment with topical steroid (betametasone) and tar preparations.

2 Patients suffered from subtotal or total alopecia, with underlying atopic dermatitis. The first was a 40 year male who had been bald for 20 years, and after treatment with the test drug for 10 months, complete regrowth of hair was observed. The second patient was a 17 old male with 2–3 years of alopecia, and treatment for 8 months with the test drug, showed only little effect.

5 Females aged from 20–49 years with Ludwig type alopecia were treated with the test drug for 6–8 months. The effect was good in 3 patients, and in 2 patients there was only a marginal effect, both showing a better response on previous treatment with minoxidil (Regain®).

5 Female patients with alopecia areata aged from 39 years to 46 years were treated for periods from 2 to 9 months, the treatment showing a very good effect.

One female 46 years old with very bad hair condition and underlying psoriasis was treated for 9 months and a very good effect on the test drug was obtained.

2 female patients aged 34 and 40 years with underlying discoid LE were successfully treated for 2 and 4 months, respectively, with a very good effect comprising regrowth of hair except for the very center of the lesion.

In conclusion, topical application of a solution comprising the sodium salt of sucrose sulfate (3% solution of sodium sucrose sulfate in a water/ethanol/propylene glycol vehicle), the solution being administered every morning and evening for time periods of 3–11 month showed to be effective in the treatment of male, androgenic alopecia and the Ludwig type alopecia in females. Furthermore, the drug was effective in the treatment of subtotal, total and aerate alopecia in patients with underlying diseases such as atopic dermatitis, psoriasis and discoid LE.

The hair-growing effect in the patients responding to the treatment was typically apparent after 1 month of treatment and in comparison to treatment with topically applied minoxidil (Regain®), the test preparation gave a markedly better effect.

EXAMPLE 16

Clinical evaluation of the prophylactic and therapeutical effect of sodium sucrose sulfate in the treatment of hair loss secondary to anti-cancer treatment. A pilot study The test preparation containing sodium sucrose sulfate from Example 11 was used both prophylactically and therapeutically in a few patients undergoing radiation and/or cytostatic anti-cancer treatment. One female started the treatment with the test preparation immediately after the anti-cancer treatment was instituted, applying the test preparation twice daily on eyebrows and eyelashes on the right side, and the left side served as untreated control. The treatment lasted four weeks. On the treated side, eyebrows and eyelashes remained but were lost on the untreated side. Another four females—also on anticancer treatment—used the test preparation twice daily, topically on the scalp after the hair was lost. A much faster regrowth of hair than normally was observed in the four females.

In conclusion, topical application of sodium sucrose sulfate as a 3% w/w solution is effective in preventing hair loss secondary to anticancer treatment and, furthermore, sodium sucrose sulfate stimulates hair regrowth after anti-cancer treatment. In addition, the results show that topically applied sodium sucrose sulfate is of beneficial use for cosmetic purposes such as for the prevention of hair loss.

EXAMPLE 17

Clinical evaluation of sucralfate in the treatment of alopecia. A pilot study

A composition containing micronized sucralfate (<5 µm, Giulini Chemie, Germany) 5%, ethanol 25%, propylene glycol 25%, and distilled water 45%, was used in two daily applications on the scalp, the composition being dispensed in a bottle with sponge applicator. The average consumption of the test preparation in individual patients was about one bottle per month. One male aged about 55 years, and with male androgenic alopecia Hamilton grade 3, used the test preparation for two months, and there was a dense regrowth of small terminal hairs in the partly balded area of the scalp. The effects were lasting after stopping the treatment for about 4 months. Another six male patients aged from 30 to 48 years, and with male androgenic alopecia Hamilton grade 3 and 4, have used the test preparation for periods of 3 months to 6 months, and in all six cases there have been a definite regrowth of terminal hairs; the effect was typically seen after 6–8 weeks of treatment. In one patient aged 50 and with total alopecia for the last 20 years, a dense regrowth of fine short terminal hairs all over the scalp was observed after application of the test preparation for 6 weeks.

It can be concluded that topical application twice daily on the scalp of 5% micronized sucralfate suspension in a water/ethanol/propylene glycol vehicle is effective in the treatment of male androgenic alopecia, also including middle aged patients.

We claim:

1. A method of treating alopecia comprising topically administering to a patient in need thereof a therapeutically effective amount of a non-esterified compound effective against alopecia selected from the group consisting of i) non-esterified, sulfated monosaccharides, ii) non-esterified, sulfated disaccharides and iii) salts and complexes of (i) or (ii) above with a substance selected from the group consisting of alkali metals, alkaline earth metals, Al, Zn, Cu, Zr, Ti, Bi, Mn and Os.

2. The method of claim 1 wherein the sulfated saccharide is at least tetrasulfated.

3. The method of claim 1 in which the compound is a non-esterified, sulfated monosaccharide, or a salt or complex thereof.

4. The method of claim 3 wherein the sulfated monosaccharide is selected from the group consisting of xylose, fructose and glucose.

5. The method of claim 4 in which the saccharide is tetrasulfated.

6. The method of claim 1 in which the compound is a non-esterified sulfated disaccharide, or a salt or complex thereof.

7. The method of claim 6 in which the sulfated disaccharide is selected from the group consisting of sucrose, lactose, maltose and cellobiose.

8. The method of claim 7 in which the disaccharide is octasulfated.

9. The method of claim 1 in which the compound does not contain a uronic acid or hexosamine residue.

10. The method of claim 6 in which the disaccharide is not obtainable by hydrolysis of chondroitin sulfate, heparin sulfate or hyaluronic acid.

11. The method of claim 1 wherein the administration is to unbroken skin of the patient.

12. A method of inhibiting the onset of alopecia, the method comprising topically administering to a patient in need thereof an inhibitory amount of a non-esterified compound effective against alopecia selected from the group consisting of i) non-estrified sulfated monosaccharides, ii) non-esterified sulfated disaccharides and iii) salts and complexes of i) or ii) above with a substance selected from the group consisting of alkali metals, alkaline earth metals, Al, Zn, Cu, Zr, Ti, Bi, Mn and Os.

13. The method of claim 12 wherein the sulfated saccharide is at least tetrasulfated.

14. The method of claim 12 in which the compound is a sulfated monosaccharide, or a salt or complex thereof.

15. The method of claim 14 wherein the sulfated monosaccharide is selected from the group consisting of xylose, fructose and glucose.

16. The method of claim 15 in which the saccharide is at least tetrasulfated.

17. The method of claim 12 in which the compound is a sulfated disaccharide, or a salt or complex thereof.

18. The method of claim 17 in which the sulfated disaccharide is selected from the group consisting of sucrose, lactose, maltose and cellobiose.

19. The method of claim 18 in which the disaccharide is octasulfated.

20. The method of claim 12 wherein the administration is to unbroken skin of the patient.

21. The method of claim 12 in which the compound does not contain a uronic acid or hexosamine residue.

22. The method of claim 17 in which the disaccharide is not obtainable by hydrolysis of chondroitin sulfate, heparin sulfate or hyaluronic acid.

23. A method of inhibiting loss of the natural color of hair, the method comprising topically administering to a patient in need thereof a cosmetically effective amount of a compound selected from the group consisting of i) sulfated monosaccharides, ii) sulfated disaccharides, iii) ester derivatives of said mono- and disaccharides, and iv) salts and complexes of said mono- and disaccharides with a substance selected from the group consisting of alkali metals, alkaline earth metals, Al, Zn, Cu, Zr, Ti, Bi, Mn and Os.

* * * * *